United States Patent [19]

Burnett

[11] Patent Number: 5,672,362
[45] Date of Patent: Sep. 30, 1997

[54] DUST MITE CONTROL METHOD USING DOT

[76] Inventor: James Burnett, P.O. Box 323, San Geronimo, Calif. 94963

[21] Appl. No.: 724,043

[22] Filed: Sep. 23, 1996

[51] Int. Cl.⁶ .................................................. A01N 59/14
[52] U.S. Cl. ..................... 424/660; 424/657; 424/658; 424/659
[58] Field of Search ..................... 424/657, 658, 424/659, 660

[56] References Cited

U.S. PATENT DOCUMENTS

| | | | |
|---|---|---|---|
| 4,374,853 | 2/1983 | Workman | 514/506 |
| 4,438,090 | 3/1984 | Brite | 424/10.31 |
| 4,688,959 | 8/1987 | Snedeker et al. | 401/283 |
| 4,988,516 | 1/1991 | Herring | 424/659 |
| 5,273,761 | 12/1993 | Kim et al. | 424/659 |
| 5,314,699 | 5/1994 | Baden | 424/660 |
| 5,587,221 | 12/1996 | McCamy et al. | 428/96 |

FOREIGN PATENT DOCUMENTS

| | | |
|---|---|---|
| 63-130509 | 6/1988 | Japan . |
| 9528164 | 10/1995 | WIPO . |

OTHER PUBLICATIONS

Caplus Abstract Accession No. 1989:187819 (1989), Asbtracting JP 63-130509 (1988).

Allergy Control Products, Inc. brochure for Acarosan dust mite powder. 1 sheet. (no publication date available).

Clinical Research in Dermatology report by Richard Halliwell, Vet M.B., Ph.D., 1987. 2 Sheets.

National Allergy Supply, Inc. article on allergy treatments. 1994. 2 sheets.

Benzyl benzoate moist powder study by Mary Hayden, RN, published in the Feb. 1992 issue of the Journal of Allergy Clinical Immunology. pp. 536–545.

1992 Rexair, Inc. reprint of various articles on dust mites. 1 sheet.

*Primary Examiner*—John Pak
*Attorney, Agent, or Firm*—Jack Lo

[57] ABSTRACT

Dust mites are a pest that is present in most homes. Their fecal pellets are known to be a significant cause of allergies. A method for controlling dust mites includes providing a 5% disodium octaborate tetrahydrate (DOT) solution, and applying it to an infested surface, such as a carpet or bedding, with a hot water vacuum. The solution is applied evenly, and is partially extracted by the vacuum on the same stroke, so that the surface is left relatively dry. The application and extraction process also cleans the surface by removing dirt and a significant number of dust mites and their fecal pellets. The residual solution kills most of the dust mites, but it poses an insignificant health exposure to humans. After drying, the applied DOT also resists removal by subsequent dry vacuuming, so that it remains effective for many weeks.

6 Claims, 2 Drawing Sheets

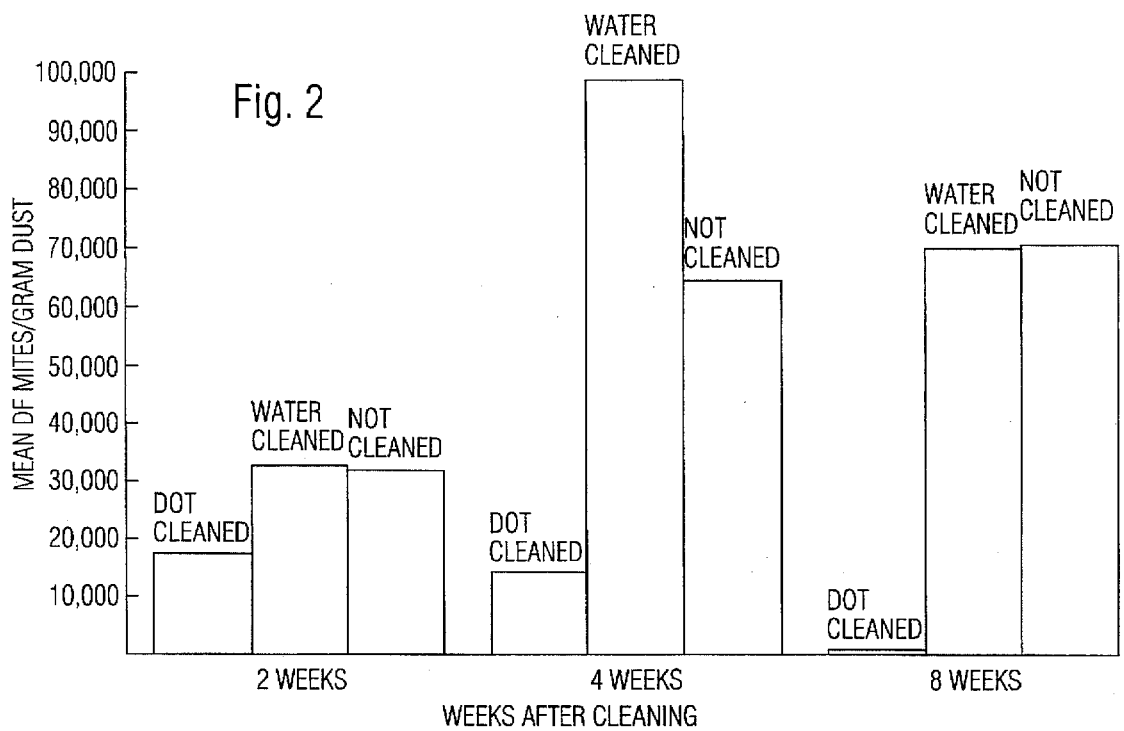
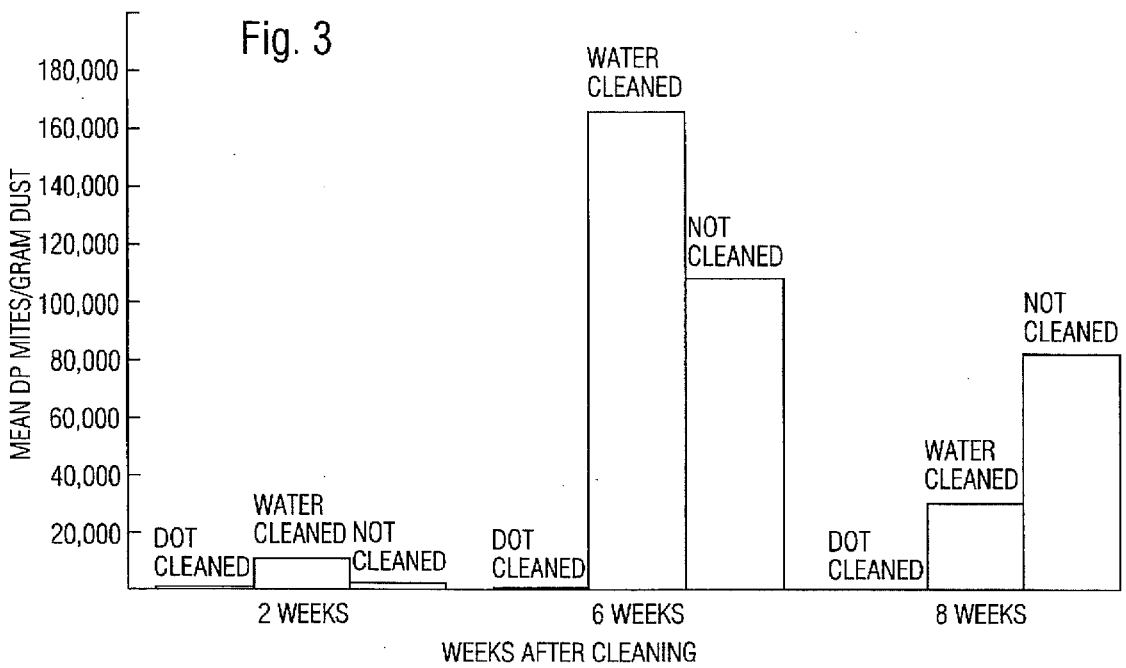

DUST MITE CONTROL METHOD USING DOT

BACKGROUND OF THE INVENTION

1. Field of the Invention

This invention relates generally to pest control methods, specifically to a dust mite control method using DOT.

2. Prior Art

Pollen is the most common and well known cause of outdoor allergies, whereas pet dander is a well known cause of indoor allergies. However, dust mites are increasing becoming known as another significant cause of indoor allergies.

Dust mites are acarids (a type of arachnid, such as spiders and scorpions) that inhabit about 90% of homes in the U.S.; they were not known to exist until 1964. They range in size between 0.1 mm and 0.5 mm. They live in all types of fibers, including carpets, clothing, fabric sofas, and bed sheets. They subsist primarily on the dead skin particles that are constantly shed by humans, and produce waste products in the form of fecal pellets. Each gram of house dust may contain up to 250,000 pellets. When the dust is stirred up by human activities, the fecal pellets are carried aloft by the dust and inhaled by people. Since their discovery, dust mite feces has been gradually recognized as an important allergen that triggers asthma and other allergy attacks. Studies have shown that reducing exposure to dust mites leads to reductions in attacks. Naturally, increasing efforts are being applied in the search for methods to kill dust mites in the domestic environment.

Various insecticides are available for controlling insects. However, acarids and insects are very different creatures. E.g., acarids have no sensory antennae, whereas insects do; acarids have four pairs of legs, whereas insects have three; acarids have a one-part body, whereas insects have three parts; acarids excrete guanine, whereas insects excrete uric acid and ammonia; and acarids have no respiratory system, whereas insects do. Therefore, different chemicals are typically required for killing acarids and insects, although some insecticides are also usable as acaricides. However, it is known that most acaricides and insecticides are ineffective in killing dust mites. Most of those that are effective must be used in concentrations that are too high to be safe for domestic applications. U.S. Pat. No. 5,314,699 to Baden discloses the use of DOT (disodium octaborate tetrahydrate) for killing fleas. However, it is commonly understood in the an that a chemical that is effective for controlling one type of pest is not necessarily effective for controlling another. Therefore, despite the long-standing demand for an effective and safe dust mite control method, DOT has not been previously used for such an application.

An acaricide sold under the trademark "Acarosan" is being marketed for killing dust mites. Its active ingredient is BB (benzyl benzoate). It is applied as a moist powder to infested areas, such as carpets and bedding. However, the moist powder tends to clump together, so that it is difficult to apply evenly. A 26 oz (0.74 kg) bag treats only 120 ft$^2$ (11.15 m$^2$), which is a relatively large amount for a relatively small room. "Acarosan" is also available as a foam, but in such form it is also difficult to apply evenly. Although the manufacturer claims that it is effective for up to six months, a study published in the February 1992 issue of the Journal of Allergy and Clinical Immunology has shown that it is effective for only a few weeks. The study has also shown that, after the moist powder is dried, it is easily removed by vacuuming, which further reduces its effectiveness. The product may also loose its acaricidal properties after prolonged storage. Furthermore, the moist powder or foam helps to dissolve dirt or other contaminants already on the surface being treated, so that when the powder or foam is dried, the dirt or contaminant becomes adhered to the surface.

OBJECTS OF THE INVENTION

Accordingly an object of the present invention is to provide a dust mite control method that is highly effective.

Another object of the present invention is to provide a dust mite control method that poses an insignificant exposure risk to humans.

Another object of the present invention is to provide a dust mite control method that resists removal by dry vacuuming, so as to remain effective for a longer period of time.

Another object of the present invention is to provide a dust mite control method that is very easy to apply evenly.

Another object of the present invention is to provide a dust mite control method that also cleans the surface being treated to remove dirt and a significant number of dust mites and their fecal pellets.

Further objects of the present invention will become apparent from a consideration of the drawings and ensuing description.

SUMMARY OF THE INVENTION

A method for controlling dust mites includes providing a 5% DOT solution, and applying it to a surface being treated with a hot water vacuum.

BRIEF DESCRIPTION OF THE DRAWINGS

FIG. 2 is a graph showing the results of an efficacy study on using DOT for controlling one type of dust mites.

FIG. 3 is a graph showing the results of an efficacy study on using DOT for controlling another type of dust mites.

DESCRIPTION—FIG. 1

Figure 1:
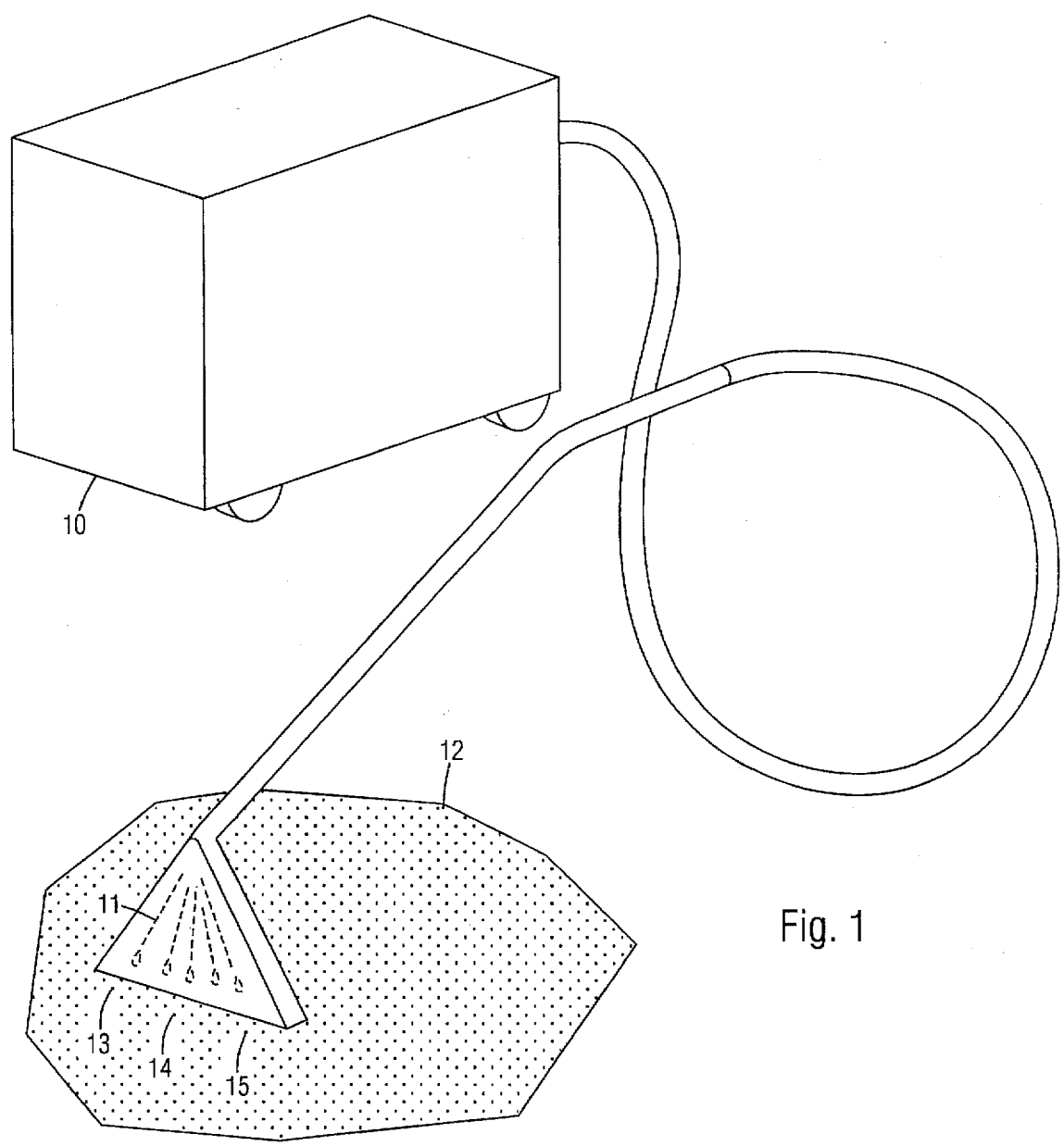
FIG. 1 is a side perspective view of a DOT solution being applied on a carpet by a conventional hot water vacuum.

A method for controlling dust mites comprises applying DOT (disodium octaborate tetrahydrate) onto areas to be treated, such as carpets, bedding, sofas, etc. As shown in FIG. 1, the DOT is preferably applied as a hot liquid solution 11 by a conventional hot water vacuum 10, commonly known as a steam carpet cleaner, onto a surface being treated, which in this example is a carpet 12. The vacuum evenly applies the solution, which penetrates carpet 12 and human skin particles 13 (dust mite food) therein. The solution also dissolves much of the dirt (not shown) and other contaminants in the carpet, and loosens dust mite fecal pellets 14. The solution may also be applied to other surfaces (not shown), including but not limited to draperies, bedding, and furniture, with separate adapters (not shown) that are typically provided with hot water vacuums.

The solution is preferably composed of DOT and hot water, which is very inexpensive and readily available, although other liquids may also be used. The concentration of DOT is preferably about 5% by weight, i.e., one unit weight of DOT powder in 20 units weight of water. A 98% DOT powder is sold under the trademark "Ecology Works Insecticide" by The Ecology Works, Inc. of San Francisco, Calif. The solution is preferably prepared by mixing 1 cup of DOT powder with 1 gallon of water. The solution is safe to handle: it has previously been proven by a study commissioned by me, and conducted at the University of California Riverside under the direction of Robert Krieger, Ph.D., to pose an insignificant exposure risk to humans. It can be easily washed off with soap and water, and it is not absorbed through the skin. Also, it does not contaminate the ambient air, and it has no unpleasant odors.

After solution 11 is sprayed onto the carpet, about ½ of the applied solution is extracted therefrom by vacuum 10, along with most of skin particles 13, dust mite fecal pellets 14, dust mites 15, and dirt and other contaminants (not shown). Much of the allergens and dirt are thus removed. Because of the vacuum action, the carpet is left relatively dry after the treatment. However, because no vacuum system is perfect, some skin particles, dust mites, and fecal pellets will remain. Such remnants are thoroughly soaked with DOT. The dust mites that remain in the carpet will eventually die from ingesting the DOT contaminated skin particles.

Because the DOT solution is soaked and worked deeply into the fibers of the carpet, it will not be removed from the carpet by regular dry vacuuming, so that it will activate, by contact, additional edible matter that is added to the carpet. Furthermore, DOT does not break down with time. Therefore, dust mite control effectiveness will remain high long after the treatment.

DESCRIPTION—FIGS. 2 AND 3

I commissioned Dr. Larry Arlian, Ph.D., of the Department of Biological Sciences and Microbiology and Immunology at Wright State University, Dayton, Ohio, to conduct a study on the efficacy of DOT as a dust mite control method. Separate studies were conducted for Dermatophagoides farinae (DF) and D. pteronyssinus (DP) dust mites. In the studies, experimental carpet pieces were inoculated with thriving, well-fed, pure DF dust mites at 1,584 mites/gram, or D. pteronyssinus (DP) dust mites at 720 mites/gram. Each study included two duplicate control sets: one duplicate was to be cleaned with water only, and the other duplicate was not cleaned.

After one week, the experimental carpet piece and one control carpet piece, both with established mite populations, were cleaned. A carpet cleaning machine, sold under the trademark BLUE LUSTER, was used to clean the control carpet with water, and to clean the experimental carpet piece at a rate of 156 ml DOT/2.5 liters water/3.07 m$^2$. Hot tap water of about 60° C. was used, which when sprayed onto the carpet, was at a temperature of about 30°–40° C. The carpets were exposed to the open air and allowed to dry indoors overnight, then they were held at 75% relative humidity and 25° C.

Triplicate samples in each set (DOT cleaned, water cleaned, and not cleaned) were assayed for live DF mites at 2, 4, and 8 weeks, and for live DP mites at 2, 6, and 8 weeks. All carpet replicates were vacuumed and the number of live (moving) mites were determined by microscopic examination of the recovered material.

The results are shown in FIGS. 2 and 3; each bar represents the average of the triplicate samples. Clearly, cleaning carpets with DOT at the tested rate greatly reduced the live populations of both DF and DP mites 4–8 weeks thereafter. After 8 weeks, DOT cleaned carpets had very low numbers of live DF and virtually no live DP mites, compared with the large number of live mites recovered from the water-cleaned or the uncleaned carpets. The effectiveness of DOT actually increases with time.

SUMMARY, VARIATIONS, AND SCOPE

Accordingly I have provided a method for applying an effective acaricide on carpets, bedding, upholstery, or any other infested surface by using a hot water vacuum. It applies the acaricide evenly and thoroughly over the surface. A large number of dust mites, their fecal pellets, and dirt are removed during application. It extracts most of the solution after application to leave the surface relatively dry. The acaricide poses an insignificant exposure risk to humans. The process is easy and economical to use, and is also long lasting.

Although the above descriptions are specific, they should not be considered as limitations on the scope of the invention, but only as examples of the preferred embodiment. Many other variations are possible within the teachings of the invention. For example, different types of carpet cleaning machines can be used. The solution can be prepared in different concentrations to suit different environmental or pest control needs. E.g., a 2.5% solution with no extraction also works. Greater than 5% concentrations also work. The solution may be heated to other temperatures, or it may be unheated. The solution may be applied with a sprayer, or it may be dusted on in powder form. The method can be used against other types of acarid or insect pests. A detergent can be combined with the acaricide solution to facilitate cleaning as well as pest control. Therefore, the reader is requested to determine the scope of the invention by the appended claims and their legal equivalents, not by the examples given.

I claim:

1. A method for controlling dust mites living on an inanimate surface comprising:

providing a liquid solution with about 2.5% by weight to about 5% by weight of dissolved disodium octaborate tetrahydrate;

heating said solution; and applying an amount of said solution which is effective to control dust mites to said surface.

2. The method of claim 1 wherein said solution is composed of said disodium octaborate tetrahydrate and water.

3. The method of claim 1 wherein said solution is applied onto said surface with a hot water vacuum.

4. The method of claim 3, further comprising partially extracting said solution from said surface after application with said hot water vacuum.

5. The method of claim 1 wherein said solution is applied onto said surface at a rate of about 0.87 liter per square meter.

6. The method of claim 1, wherein the heating step comprises heating said solution to about 60° C.

\* \* \* \* \*